United States Patent
Johnson et al.

(10) Patent No.: US 6,342,246 B2
(45) Date of Patent: *Jan. 29, 2002

(54) IMAGE FORMS AND METHOD FOR AMELIORATING MALE ERECTILE DYSFUNCTION

(75) Inventors: Edward Stewart Johnson, Ruscombe; Anthony Clarke, Henley-on-Thames; Richard David Green, Marlborough, all of (GB)

(73) Assignee: R.P. Scherer Limited (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/352,515

(22) Filed: Jul. 12, 1999

Related U.S. Application Data

(63) Continuation of application No. PCT/GB98/00143, filed on Jan. 16, 1998.

(30) Foreign Application Priority Data

Jan. 17, 1997 (GB) .............................................. 9700878

(51) Int. Cl.[7] .............................. A61K 9/20; A61K 9/14; A61K 31/56; A61K 31/44; A01N 43/42
(52) U.S. Cl. ...................... 424/464; 424/434; 424/435; 424/484; 424/485; 424/486; 424/489; 514/179; 514/282; 514/284; 514/289
(58) Field of Search ................................ 424/464, 434, 424/435, 484, 485, 486, 488; 514/289; 515/282, 284, 179

(56) References Cited

U.S. PATENT DOCUMENTS

| | | | |
|---|---|---|---|
| 3,928,566 A | | 12/1975 | Briggs |
| 4,098,802 A | * | 7/1978 | Van Der Vies .......... 260/397.4 |
| 4,877,774 A | * | 10/1989 | Pitha et al. .................... 514/26 |
| 5,135,752 A | * | 8/1992 | Snipes ......................... 424/435 |
| 5,529,789 A | * | 6/1996 | Lo .............................. 424/473 |
| 5,576,014 A | * | 11/1996 | Mizumoto et al. .......... 424/435 |

FOREIGN PATENT DOCUMENTS

| | | | |
|---|---|---|---|
| GB | 1548022 A | | 7/1979 |
| WO | 95/20377 A | | 8/1995 |
| WO | 95/28930 | * | 11/1995 |
| WO | 95/28930 A | | 11/1995 |
| WO | 95 28930 | * | 11/1995 |
| WO | WO-95/28930 | * | 11/1995 |
| WO | 96/41619 A | | 12/1996 |
| WO | 97/06786 | * | 2/1997 |
| WO | 97/06786 A | | 2/1997 |
| WO | 97 06786 | * | 2/1997 |

OTHER PUBLICATIONS

Bonuccelli et al Naloxone partly counteracts apomorphine side effects Chlin Neuropharm. 14(5):442–449 1991.*

(List continued on next page.)

Primary Examiner—Thurman K. Page
Assistant Examiner—Todd D Ware
(74) Attorney, Agent, or Firm—Donald D. Nickey; Andrew G. Rozycki; Monique A. Momeault

(57) ABSTRACT

The use of a pharmaceutical composition for oral administration comprising a carrier and active ingredient selected from a dopamine agonist, testosterone and mixtures thereof, the composition being in the form of a fast-dispersing dosage form designed to release the active ingredient rapidly in the oral cavity for the manufacture of a medicament for treatment of male erectile dysfunction.

16 Claims, 1 Drawing Sheet

OTHER PUBLICATIONS

Durif et al Relation between clinical efficacy and pharmacokinetic parameters after sublingual apomorphine in Parkinson's disease Clinical Neuropharmacology 16(2);157–166, Apr. 1993.*

Bonuccelli et al Naloxone partly counteracts apomorphine side effects Clinical Neuropharmacology 14(5);442–449, 1991.*

Durif et al Relation between clinical efficacy and pharmacokinetic parameters after sublingual apomorphine in parkinson's disease Clin Neuropharm 16(2):157–166 1993.*

Bonuccelli et al Naloxone partly counteracts apomorphine side effects Clin Neuropharm. 14(5):442–449 1991.*

Database Medline U.S. National Library of Medicine (NLM), Bethesda, MD US Accession No. 95159287, XP00206017 (abstract).

J. P. Heaton et al. "Recovery of Erectile Function by the Oral Administration of Apomorphine," *Urology,* vol. 45 No. 2, 1995 (pp. 200–206).

* cited by examiner

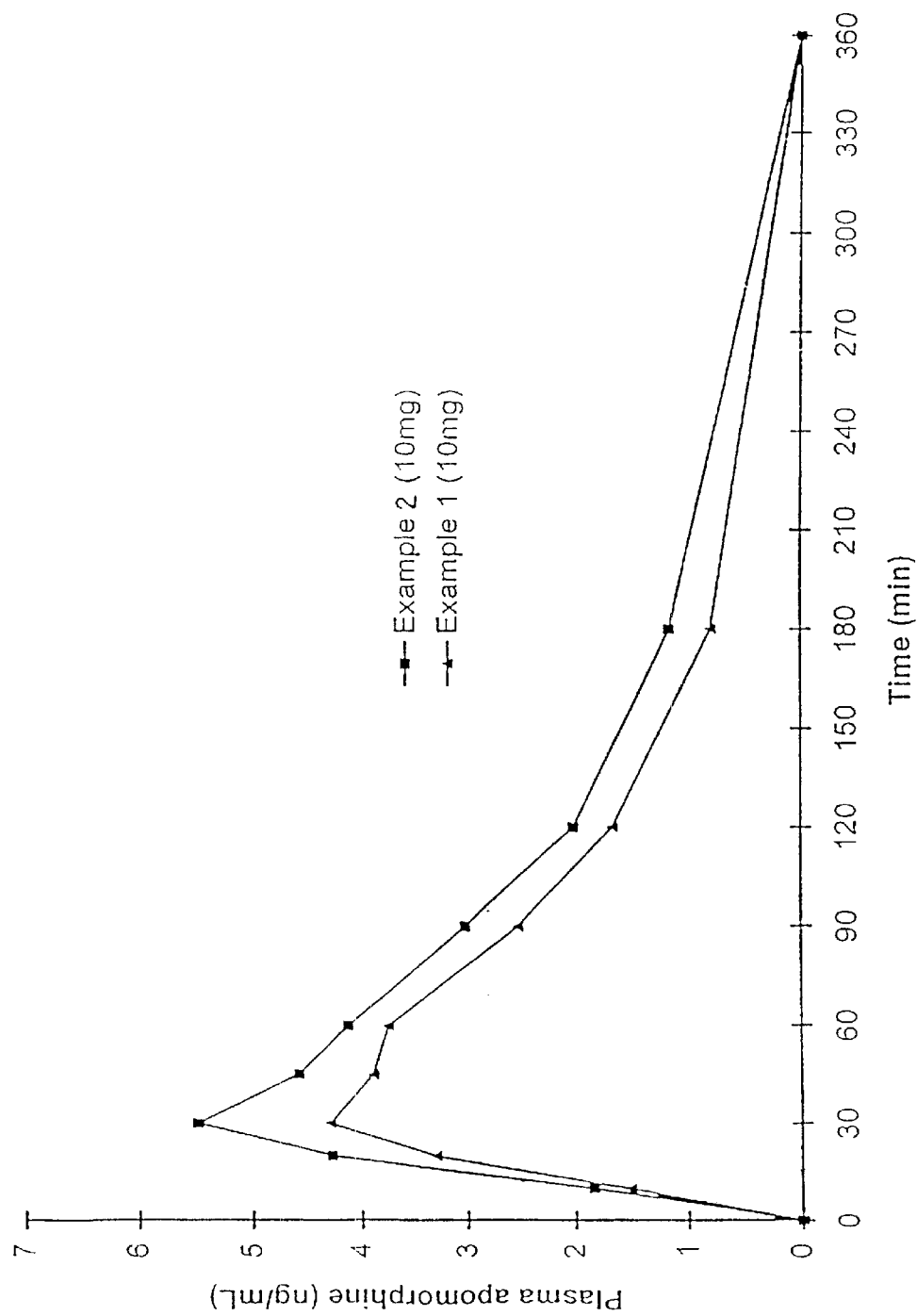

IMAGE FORMS AND METHOD FOR AMELIORATING MALE ERECTILE DYSFUNCTION

RELATED APPLICATIONS

This application is a continuation of International Patent Application PCT/GB98/00143 filed Jan. 16, 1998, now WO 98/31368 based on Great Britain Patent Application GB9700878.3 filed on Jan. 17, 1997.

FIELD OF THE INVENTION

This invention relates to dosage forms and methods for ameliorating erectile dysfunction in male patients. More particularly, this invention relates to the use of fast-dispersing dosage forms of drugs for amelioration of erectile dysfunction in male patients.

BACKGROUND OF THE INVENTION

A normal erection occurs as a result of a coordinated vascular event in the penis. This is usually triggered neurally and consists of vasodilatation and smooth muscle relaxation in the penis and its supplying arterial vessels. Arterial inflow causes enlargement of the substance of the corpora cavernosa. Venous outflow is trapped by this enlargement, permitting sustained high blood pressures in the penis sufficient to cause rigidity. Muscles in the perineum also assist in creating and maintaining penile rigidity. Erection may be induced centrally in the nervous system by sexual thoughts or fantasy, and is usually reinforced locally by reflex mechanisms.

Male erectile dysfunction (MED) is defined as the inability to achieve and sustain an erection sufficient for intercourse. In any given case this can result from psychological disturbances (psychogenic), from physiological abnormalities in general (organic), from neurological disturbances (neurogenic), hormonal deficiencies (endocrine) or from a combination of the foregoing.

The effect of apomorphine on penile tumescence in male patients has been studied. These studies show that while apomorphine can indeed induce an erection in a psychogenic male patient, the apomorphine dose required to achieve a significant erectile response is usually accompanied by nausea or other serious undesirable side effects such as hypertension, flushing and diaphoresis. The specific mechanisms by which apomorphine acts to produce an erectile response in a human patient are not yet completely understood, however.

Moreover, apomorphine has been shown to have very poor oral bioavailability. See, for example, Baldessarini et al., in Gessa et al., eds., *Apomorphine and Other Dopaminomimetics, Basic Pharmacology*, Vol. 1, Raven Press, N.Y. (1981), pp. 219–228.

WO95/28930 discloses sublingual apomorphine dosage forms, usually containing about 2.5 to about 10 milligrams of apomorphine, and dissolving in water within a time period of at least about 2 minutes but less than about 10 minutes, preferably about 3 minutes to about 5 minutes, have been found to be effective in male patients suffering from psychogenic erectile dysfunction for the induction and maintenance of an erection sufficient for intercourse (i.e. vaginal penetration) without nausea or other undesirable side effects. The apomorphine is administered sublingually, preferably about 15 to 20 minutes prior to sexual activity, and so as to maintain a predetermined circulating serum levels and mid-brain tissue levels of apomorphine during the period of sexual activity.

The foregoing sublingual apomorphine dosage forms are also suitable for screening patients complaining of erectile dysfunction so as to identify patients of psychogenic etiology.

PCT/GB96/02020 discloses a pharmaceutical composition for oral administration comprising a carrier and, as active ingredient, a dopamine agonist, in which the composition is in the form of a fast-dispersing dosage form designed to release the active ingredient rapidly in the oral cavity.

It was found that such fast-dispersing dosage forms promote pre-gastric absorption of the active ingredient, that is, absorption of the active ingredient from that part of the alimentary canal prior to the stomach. The term "pre-gastric absorption" thus includes buccal, sublingual, oropharyngeal and oesophageal absorption. Dopamine agonists absorbed by such pre-gastric absorption pass straight into the systemic circulatory system thereby avoiding first pass metabolism in the liver. Accordingly, bioavailability of dopamine agonists absorbed in this way may also be increased. This means that the dose of such dopamine agonists may be reduced whilst still producing the desired beneficial effects and this decrease in dose will result in a corresponding reduction of unwanted side effects.

The pharmaceutical compositions disclosed in PCT/GB96/02020 were developed for the treatment and/or evaluation of Parkinson's disease.

SUMMARY OF THE INVENTION

It has now been found that fast-dispersing dosage forms containing a dopamine agonist, such as apomorphine, may be used to treat male erectile dysfunction.

According to the present invention there is provided a pharmaceutical composition for oral administration for the treatment of male erectile dysfunction comprising a carrier and active ingredient comprising a dopamine agonist, testosterone or mixtures thereof, the composition being in the form of a fast-dispersing dosage form designed to release the active ingredient rapidly in the oral cavity.

The use of a fast-dispersing dosage form has several advantages over the use of conventional sublingual tablets.

The efficiency of the fast-dispersing dosage form allows low doses to be employed thereby reducing undesirable side effects, particularly nausea and vomiting.

The dosage form acts more quickly than sublingual tablets which allows the dose to be taken when it is required rather than a considerable time before sexual activity. This is both psychologically and socially preferable to sucking a tablet for several minutes in advance of sexual activity.

There is a faster offset of action since the active ingredient is rapidly absorbed rather than absorbed over a prolonged period of time. The faster offset avoids painful persistent erection.

The rapid onset and offset of action is less likely to induce tolerance to the dopamine agonist.

DETAILED DESCRIPTION OF THE INVENTION

One example of a fast-dispersing dosage form is described in U.S. Pat. No. 4,855,326 in which a melt spinnable carrier agent, such as sugar, is combined with an active ingredient and the resulting mixture spun into a "candy-floss" preparation. The spun "candy-floss" product is then compressed into a rapidly dispersing, highly porous solid dosage form.

U.S. Pat. No. 5,120,549 discloses a fast-dispersing matrix system which is prepared by first solidifying a matrix-forming system dispersed in a first solvent and subsequently contacting the solidified matrix with a second solvent that is substantially miscible with the first solvent at a temperature lower than the solidification point of the first solvent, the matrix-forming elements and active ingredient being substantially insoluble in the second solvent, whereby the first solvent is substantially removed resulting in a fast-dispersing matrix.

U.S. Pat. No. 5,079,018 discloses a fast-dispersing dosage form which comprises a porous skeletal structure of a water soluble, hydratable gel or foam forming material that has been hydrated with water, rigidified in the hydrated state with a rigidifying agent and dehydrated with a liquid organic solvent at a temperature of about 0° C. or below to leave spaces in place of hydration liquid.

Published International Application No. WO 93/12769 (PCT/JP93/01631) describes fast-dispersing dosage forms of very low density formed by gelling, with agar, aqueous systems containing the matrix-forming elements and active ingredient, and then removing water by forced air or vacuum drying.

U.S. Pat. No. 5,298,261 discloses fast-dispersing dosage forms which comprise a partially collapsed matrix network that has been vacuum-dried above the collapse temperature of the matrix. However, the matrix is preferably at least partially dried below the equilibrium freezing point of the matrix.

Published International Application No. WO 91/04757 (PCT/US90/05206) discloses fast-dispersing dosage forms which contain an effervescent disintegration agent designed to effervesce on contact with saliva to provide rapid disintegration of the dosage form and dispersion of the active ingredient in the oral cavity.

U.S. Pat. No. 5,595,761 discloses a particulate support matrix for use in making a rapidly dissolving tablet, comprising:

a first polypeptide component having a net charge when in solution, e.g. non-hydrolysed gelatin;

a second polypeptide component having a net charge of the same sign as the net charge of the first polypeptide component when in solution e.g. hydrolysed gelatin; and a bulking agent, and wherein the first polypeptide component and the second polypeptide component together comprise about 2% to 20% by weight of the particulate support matrix and wherein the bulking agent comprises about 60% to 96% by weight of the particulate support matrix; and wherein the second polypeptide component has a solubility in aqueous solution greater than that of the first polypeptide component and wherein the mass:mass ratio of the first polypeptide component to the second polypeptide component is from about 1:1/2 to about 1:14; and wherein when the support matrix is introduced into an aqueous environment the support matrix is disintegrable within less than about 20 seconds.

The term "fast-dispersing dosage form" therefore encompasses all the types of dosage form described in the preceding paragraphs. However, it is particularly preferred that the fast-dispersing dosage form is of the type described in U.K. Patent No. 1548022, that is, a solid fast-dispersing dosage form comprising a network of the active ingredient and a water-soluble or water-dispersible carrier which is inert towards the active ingredient, the network having been obtained by subliming solvent from a composition in the solid state, that composition comprising the active ingredient and a solution of the carrier in a solvent.

It is preferred that the composition of the invention disintegrates within 1 to 60 seconds, more preferably 1 to 30 seconds, especially 1 to 10 seconds and particularly 2 to 8 seconds, of being placed in the oral cavity.

In the case of the preferred type of fast-dispersing dosage form described above, the composition will preferably contain, in addition to the active ingredient, matrix forming agents and secondary components. Matrix forming agents suitable for use in the present invention include materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; and polypeptide/protein or polysaccharide complexes such as gelatin-acacia complexes.

Other matrix forming agents suitable for use in the present invention include sugars such as mannitol, dextrose, lactose, galactose and trehalose; cyclic sugars such as cyclodextrin; inorganic salts such as sodium phosphate, sodium chloride and aluminium silicates; and amino acids having from 2 to 12 carbon atoms such as glycine, L-alanine, L-aspartic acid, L-glutamic acid, L-hydroxyproline, L-isoleucine, L-leucine and L-phenylalanine.

One or more matrix forming agents may be incorporated into the solution or suspension prior to solidification. The matrix forming agent may be present in addition to a surfactant or to the exclusion of a surfactant. In addition to forming the matrix, the matrix forming agent may aid in maintaining the dispersion of any active ingredient within the solution or suspension. This is especially helpful in the case of active agents that are not sufficiently soluble in water and must, therefore, be suspended rather than dissolved.

Secondary components such as preservatives, antioxidants, surfactants, viscosity enhancers, colouring agents, flavouring agents, pH modifiers, sweeteners or taste-masking agents may also be incorporated into the composition. Suitable colouring agents include red, black and yellow iron oxides and FD & C dyes such as FD & C blue No. 2 and FD & C red No. 40 available from Ellis & Everard. Suitable flavouring agents include mint, raspberry, liquorice, orange, lemon, grapefruit, caramel, vanilla, cherry and grape flavours and combinations of these. Suitable pH modifiers include citric acid, tartaric acid, phosphoric acid, hydrochloric acid and maleic acid. Suitable sweeteners include aspartame, acesulfame K and thaumatin. Suitable taste-masking agents include sodium bicarbonate, ion-exchange resins, cyclodextrin inclusion compounds, adsorbates or microencapsulated actives.

It is preferred that the dopamine agonist is selected from 5,6,6a,7-tetrahydro-6-methyl-4H-dibenzo[de,g]quinoline-10,11-diol(apomorphine),5,6,6a,7-tetrahydro-6-propyl-4H-dibenzo[de,g]quinoline-10,11-diol(N-propylnoraporphine), (5'α)-2-bromo-12'-hydroxy-2'-(1-methylethyl)-5'-(2-methylpropyl)ergotaman-3',6',18-trione(bromocriptine), 1-[(6-allylergolin-8β-yl)carbonyl]-1-[3-(dimethylamino) propyl]-3-ethylurea (cabergoline), N'-[(8α)-9,10-didehydro-6-methylergolin-8-yl]-N,N-diethylurea (lisuride), [[(8β)-1, 6-dimethylergolin-8-yl]methyl]-carbamic acid phenylmethyl ester (metergoline), (4aR)-trans-3,4,4a,5,6, 10b-hexahydro-4-propyl-2H-naphth[1,2-b]-1,4-oxazin-9-ol (naxagolide), 8-[(methylthio)methyl]-6-propylergoline (pergolide), 2-[4-(1,3-benzodioxol-5-ylmethyl)-1- piperazinyl]pyrimidine (piribedil), 4-[2-(dipropylamino)
ethyl]indolin-2-one (ropinirole), N,N-diethyl-N'-[(8α)-6-
methylergolin-8-yl]urea (terguride) and (±)-N,N-diethyl-N'-
[(3R,4aR*,10aS*)-1,2,3,4,4a,5,10,10a-octahydro-6-
hydroxy-1-propylbenzo[g]quinolin-3-yl]sulphamide
(quinagolide) salts thereof and mixtures thereof. More
preferably, the dopamine agonist is apomorphine or a salt,
preferably an acid-addition salt, thereof, especially the
hydrochloride salt.

It is also preferred that the dopamine agonist is present in
the composition in an amount from 0.05 to 10 mg, preferably
0.05 to 5 mg.

The ability of dopamine receptor agonists to cause penile
erections in rodents has been reported in a review by Lal
(Prog. Neuro-Psychopharmacol. & Biol. Psychiat., 1988,
vol 12, pp. 117–164). It has been said that dose, and
presumably plasma concentration, is critical with low doses
of apomorphine or bromocriptine more effective than higher
doses. It has been postulated that the physiological response
is mediated through activation of central D2 receptors, since
it has been shown that domperidone, a peripheral dopamine
antagonist, does not interfere with this response. It is thus
believed that plasma levels of apomorphine which induce
dopamine receptor stimulation in Parkinsonian patients
should also be effective in the treatment of male erectile
dysfunction. However, the adverse side-effects, seen with
apomorphine, of nausea, hypotension and sedation should be
minimised by the use of as low a dose as possible.

Heaton et al, (1995), Urology, 45 : 200–206 reports
patients with MED were given apomorphine liquid sub-
lingually (doses of 10 mg and 20 mg), a sub-lingual tablet
(5 mg) or a slow-dissolving sub-lingual tablet (3 mg and 4
mg). Plasma levels were not recorded, but all doses and
dosage forms were active, although side effects were a
problem in some groups.

Van Laar et al, 1996, Movement Disorders, 11: 634–638
reported peak plasma levels after administration of sub-
lingual apomorphine tablets (10 mg). The peak plasma
levels (ng/ml) were 7.0±0.8 in one experiment and 7.4±1.0
in another. In a third experiment, the sub-lingual tablets were
acidified with ascorbic acid—the plasma level reduced
slightly to 4.3±1.5.

Since efficacy in the Heaton et al paper was seen with
doses as low as 3 mg, the peak plasma level to achieve this
(based on dose-corrected data from the van Laar paper)
would be around 1.3 to 2.2 ng/ml.

A study on the therapeutic window of apomorphine in 3
groups of Parkinsonian patients, by the use of stepwise
administration of apomorphine by intravenous infusion,
demonstrated that it is possible to separate the onset of
pharmacological activity and side-effects. Clinical efficacy,
in the treatment of symptoms of Parkinson's disease, was
seen at mean serum apomorphine levels above 3.8–5.0
ng/ml whilst adverse effects were seen at mean serum
apomorphine levels above 12.2–18.5 ng/ml.

These reports would suggest that treatment of MED with
apomorphine should generally aim for plasma levels of at
least 1 to 5 ng/ml and should not be allowed to exceed 10
ng/ml.

The precise quantity of active ingredient will depend on
the dopamine agonist chosen. Typical dose ranges for the
dopamine agonists mentioned above are as follows:

| | |
|---|---|
| Apomorphine | 1–20 mg, preferably 1–10 mg |
| N-propylnoraporphine | 1–20 mg, preferably 1–10 mg |
| Bromocriptine | 0.5–10 mg, preferably 0.5–5 mg |
| Cabergoline | 0.05–2 mg, preferably 0.05–0.5 mg |
| Lisuride | 0.05–2 mg, preferably 0.05–0.4 mg |
| Metergoline | 4–20 mg, preferably 4–8 mg |
| Naxagolide | 0.1–10 mg, preferably 0.1–5 mg |
| Pergolide | 0.05–1 mg, preferably 0.05–0.5 mg |
| Piribedil | 1–20 mg, preferably 1–10 mg |
| Ropinirole | 0.25–20 mg, preferably 0.25–5 mg |
| Terguride | 1–10 mg, preferably 1–5 mg |
| Quinagolide | 0.1–5 mg, preferably 0.1–1 mg |

Dopamine agonists may produce side effects such as
nausea and vomiting. The composition used in the invention
may be administered in conjunction with an anti-emetic. The
anti-emetic may be conveniently administered in the same
composition as the dopamine agonist.

Alternatively, the anti-emetic may be administered sepa-
rately from the dopamine agonist by any of the usual oral or
parenteral routes of administration, for instance, by tablets,
capsules, suspensions, suppositories, infusions, injections,
etc., at a suitable time which may be before, after or
simultaneously with administration of the dopamine agonist.
It is particularly preferred that the anti-emetic is formulated
in a fast-dispersing dosage form of the type described above
as it is envisaged that such a fast-dispersing dosage form of
the anti-emetic would have many of the advantages associ-
ated with such formulations, such as increased
bioavailability, dose reduction, ease of administration etc. as
described above, although the precise advantages observed
will depend on the nature of the anti-emetic chosen.

It is preferred that the anti-emetic is present in the
composition in an amount of from 1 to 60 mg. However, the
precise quantity of anti-emetic to be administered to the
patient will depend on the anti-emetic that is selected.
Suitable anti-emetics include anti-histamines, such as tri-
methobenzamide; peripheral dopamine antagonists, such as
5-chloro-1-[1-[3-(2,3-dihydro-2-oxo-1H-benzimidazol-1-
yl)propyl]-4-piperidinyl]-1,3-dihydro-2H-benzimidazol-2-
one(domperidone) and salts thereof, and serotonin (5-HT$_3$)
receptor antagonists, such as endo-1-methyl-N-(9-methyl-9-
azabicyclo[3.3.1]non-3-yl)-1H-indazole-3-carboxamide
(granisetron), 1,2,3,9-tetrahydro-9-methyl-3-[(2-methyl-
1H-imidazol-1-yl)methyl]-4H-carbazol-4-one
(ondansetron) and 1αH,5αH-tropan-3α-yl indole-3-
carboxylate (tropisetron) and salts thereof. Of these, dom-
peridone is especially preferred.

Typical dose ranges for the anti-emetics mentioned above
are as follows:

| | |
|---|---|
| Domperidone | 20–120 mg, preferably 30–60 mg |
| Granisetron | 1–10 mg, preferably 1–3 mg |
| Ondansetron | 4–32 mg, preferably 4–8 mg |
| Tropisetron | 1–10 mg, preferably 1–5 mg |
| N-[p[2-(dimethylamino)-ethoxy]benzyl]-3,4,5,trimethoxybenzamide | 750–1000 mg |

Apomorphine is an opium alkaloid. Thus, as mentioned
above, when apomorphine or another opium alkaloid or
synthetic derivative is selected as the dopamine agonist,
further side-effects, such as sedation, respiratory depression,
hypotension, bradycardia, sweating and yawning may be
produced. However, it has been found that all these side-effects can be treated by administration of an opioid antagonist in conjunction with the opioid dopamine agonist. The opioid antagonist may be conveniently administered in the same composition as the dopamine agonist. Thus, such a composition may also include an anti-emetic in addition to the dopamine agonist and opioid antagonist although this is not essential since the opioid antagonist also counteracts some of the emetic effects of the dopamine agonist. Alternatively, the opioid antagonist may be administered separately from the dopamine agonist by any of the usual oral or parenteral routes of administration at a suitable time which may be before, after or simultaneously with administration of the dopamine agonist. It is particularly preferred that the opioid antagonist is formulated in a fast-dispersing dosage form of the type described above as it is envisaged that such a fast-dispersing dosage form of the opioid antagonist would exhibit many of the advantages associated with such formulations, such as increased bioavailability, dose reduction, ease of administration etc. as described above, although the precise advantages observed will depend on the nature of the opioid antagonist chosen.

It is preferred that the opioid antagonist is present in the composition in an amount of from 0.5 to 100 mg, more preferably 0.5 to 50 mg. However, the precise quantity of opioid antagonist to be administered to the patient will depend on the opioid antagonist that is chosen. Suitable opioid antagonists include 4,5-epoxy-3,14-dihydroxy-17-(2-propenyl)morphinan-6-one(naloxone) and 17-(cyclopropylmethyl)-4,5-epoxy-3,14-dihydroxymorphinan-6-one (naltrexone) and salts, particularly acid-addition salts and, especially, the hydrochloride, thereof. A typical dose range for naloxone is 0.25–10 mg, and for naltrexone is 10–100 mg.

Alteration in endocrine function represents about one third of the total organic causes of male erectile dysfunction as reported in Aversa A et al, 1995, Mol Androl 7, 3–4. The administration of testosterone in the fast-dispersing dosage form assists in ameliorating this condition. A typical dosage range for oral administration of testosterone is 10 to 100 mg, preferably 10 to 50 mg. The composition may contain testosterone alone or in combination with a dopamine agonist.

The invention is further illustrated by the following Examples.

EXAMPLE 1
Preparation of a Fast-dispersing Dosage Form of Apomorphine (a) Preparation of Apomorphine Hydrochloride 2.0% Dispersion Gelatin (792 g) and mannitol (594 g) were dispersed in a portion of purified water (16 kg) by mixing thoroughly in the bowl of a vacuum mixer. The mix was then heated to 40° C.±20° C. and homogenised for ten minutes. The mix was cooled down to room temperature (20–24° C.). When cooled the apomorphine hydrochloride (360 g) was added. The mix was homogenised to ensure dissolution of the drug. Citric acid (166.32 g) was added gradually with stirring, to adjust the solution pH to 3.0. The remaining water (87.68 g) was added to the mixer and the bulk mix homogenised to ensure dissolution was complete.

(b) Preparation of Apomorohine Hydrochloride 10 mg Units 500 mg of the apomorphine hydrochloride 2.0% dispersion formed in (a) above was dosed into each one of a series of pre-formed blister pockets having a pocket diameter of 16 mm. The blister laminate comprised 200 μm PVC coated with 40 g per square metre PVdC. The product was frozen immediately in a liquid nitrogen freeze tunnel. The frozen product was then stored below −20° C. for a minimum of 12 hours prior to freeze-drying in a freeze drier using a drying temperature of +10° C. and a chamber pressure of 0.5 mbar. The freeze dried units were then inspected for the presence of critical defects and the remainder of the batch sealed with lidding foil consisting of a paper/foil laminate (20 μm aluminium). Each blister was then coded with a batch number and overwrapped in a preformed sachet by placing the blister in the sachet and sealing the open end of the sachet completely. Each sachet was then labelled with the product name, batch number, date of manufacture and suppliers name.

| Ingredient | Parts by Weight | % by weight of composition |
|---|---|---|
| Purified water USP/EP* | 446.880 | 89.4 |
| Apomorphine HCl BP/EP | 10.000 | 2.0 |
| Gelatin EP/USNF | 22.000 | 4.4 |
| Mannitol EP/USP | 16.500 | 3.3 |
| Citric Acid EP/USP | 4.620 | 0.9 |
| Total (pH = 3) | 500.000 | 100.0 |

*Signifies removed during the lyophilisation process.

EXAMPLE 2

The following formulation was prepared using the process described in Example 1.

| Ingredient | Parts by Weight | % by weight of composition |
|---|---|---|
| Purified water EP/USP* | 433.000 | 86.60 |
| Apomorphine HCl BP/EP | 10.000 | 2.0 |
| Gelatin EP/USNF | 25.000 | 5.0 |
| Mannitol EP/USP | 20.000 | 4.0 |
| Glycine USP | 10.000 | 2.0 |
| Citric Acid EP/USP | 2.000 | 0.40 |
| Total (pH = 4) | 500.000 | 100.00 |

*signifies removed during lyophilisation process.

EXAMPLE 3
Comparative Pharmacokinetic Study

The objective of this study was to compare the bioavailability of different fast dispersing formulations of apomorphine hydrochloride, prepared by the method of Example 1, following administration to six healthy volunteers.

Due to the emetic properties of apomorphine, subjects were pre-treated with the anti-emetic domperidone. Following two days of domperidone pre-treatment, subjects were randomised to receive the following apomorphine treatments:

10 mg Apomorphine HCl (one unit of Example 1)
10 mg Apomorphine HCl (one unit of Example 2)

Blood samples for pharmacokinetic analysis were taken pre-dose and at intervals for six hours after each dose of apomorphine. The results are reported in FIG. 1 of the accompanying drawings. It will be seen that apomorphine is rapidly absorbed from both formulations of the fast-dispersing dosage form, reaching a maximum concentration in plasma after about 30 minutes.

The following examples further exemplify formulations which can be prepared using the process described in Example 1:

EXAMPLE 4

| Ingredient | Parts by Weight | % by weight of composition |
|---|---|---|
| Purified Water EP/USP* | 438.500 | 87.70 |
| Apomorphine HCl BP/EP | 10.000 | 2.00 |
| Gelatin EP/USNF | 25.000 | 5.00 |
| Mannitol EP/USP | 20.000 | 4.00 |
| Citric Acid EP/USP | 1.500 | 0.30 |
| Aspartame EP/USNF | 2.500 | 0.50 |
| Peppermint Flavour | 2.500 | 0.50 |
| Total | 500.000 | 100.00 |

*signifies removed during lyophilisation process.

EXAMPLE 5

| Ingredient | Parts by Weight | % by weight of composition |
|---|---|---|
| Purified Water EP/USP* | 215.000 | 86.00 |
| Apomorphine HCl BP/EP | 10.000 | 4.00 |
| Gelatin EP/USNF | 11.500 | 4.60 |
| Mannitol EP/USP | 10.000 | 4.00 |
| Citric Acid EP/USP | 1.500 | 0.60 |
| Aspartame EP/USNF | 2.000 | 0.80 |
| Total | 250.000 | 100.00 |

*signifies removed during lyophilisation process.

EXAMPLE 6

| Ingredient | Parts by Weight | % by weight of composition |
|---|---|---|
| Purified Water EP/USP* | 441.000 | 88.20 |
| Apomorphine HCl BP/EP | 10.000 | 2.00 |
| Gelatin EP/USNF | 25.000 | 5.00 |
| Mannitol EP/USP | 20.000 | 4.00 |
| Citric Acid EP/USP | 1.500 | 0.30 |
| Aspartame EP/USNF | 2.500 | 0.50 |
| Total | 500.000 | 100.00 |

*signifies removed during lyophilisation process.

EXAMPLE 7

| Ingredient | Parts by Weight | % by weight of composition |
|---|---|---|
| Purified Water EP/USP* | 425.000 | 85.00 |
| Apomorphine HCl BP/EP | 10.000 | 2.00 |
| Domperidone | 20.000 | 4.00 |
| Gelatin EP/USNF | 20.000 | 4.00 |
| Mannitol EP/USP | 15.000 | 3.00 |
| Giycine USP | 5.000 | 1.00 |
| Aspartame EP/USNF | 2.500 | 0.50 |
| Peppermint Flavour | 2.500 | 0.50 |
| Total | 500.000 | 100.00 |

*signifies removed during lyophilisation process.

EXAMPLE 8

| Ingredient | Parts by Weight | % by weight of composition |
|---|---|---|
| Purified Water EP/USP* | 138.2500 | 92.1667 |
| Lisuride Maleate | 0.2000 | 0.1333 |
| Gelatin EP/USNF | 6.0000 | 4.0000 |
| Mannitol EP/USNF | 4.5000 | 3.0000 |
| Aspartame EP/USNF | 0.3000 | 0.2000 |
| Cherry Flavour | 0.7500 | 0.5000 |
| Total | 150.000 | 100.0000 |

*signifies removed during lyophilisation process.

EXAMPLE 9

| Ingredient | Parts by Weight | % by weight of composition |
|---|---|---|
| Purified Water EP/USP* | 138.9500 | 92.6333 |
| Pergolide Mesylate | 0.2500 | 0.1667 |
| Gelatin EP/USNF | 6.0000 | 4.0000 |
| Mannitol EP/USP | 4.5000 | 3.0000 |
| Aspartame EP/USNF | 0.3000 | 0.2000 |
| Total | 150.0000 | 100.0000 |

*signifies removed during lyophilisation process.

EXAMPLE 10

| Ingredient | Parts by Weight | % by weight of composition |
|---|---|---|
| Purified Water EP/USP* | 226.250 | 90.50 |
| Bromocriptine Mesylate | 2.500 | 1.00 |
| Gelatin EP/USNF | 10.000 | 4.00 |
| Mannitol EP/USP | 7.500 | 3.00 |
| Aspartame EP/USNF | 1.250 | 0.50 |
| Cherry Flavour | 1.250 | 0.50 |
| Peppermint Flavour | 1.250 | 0.50 |
| Total | 250.000 | 100.00 |

*signifies removed during lyophilisation process.

EXAMPLE 11

| Ingredient | Parts by Weight | % by weight of composition |
|---|---|---|
| Purified Water EP/USP* | 137.750 | 91.8333 |
| Ropinirole | 1.000 | 0.6667 |
| Gelatin EP/USNF | 6.000 | 4.0000 |
| Mannitol EP/USP | 4.500 | 3.0000 |
| Aspartame EP/USNF | 0.750 | 0.5000 |
| Total | 150.000 | 100.0000 |

*signifies removed during lyophilisation process.

EXAMPLE 12

| Ingredient | Parts by Weight | % by weight of composition |
|---|---|---|
| Purified Water EP/USP* | 431.500 | 86.30 |
| Apomorphine HCl BP/EP | 10.000 | 2.00 |
| Naloxone HCl BP/EP | 10.000 | 2.00 |
| Gelatin EP/USNF | 20.500 | 4.10 |
| Mannitol EP/USP | 15.000 | 3.00 |
| Citric Acid EP/USP | 1.500 | 0.30 |
| Aspartame EP/USNF | 3.000 | 0.60 |
| Grapefruit Flavour | 1.000 | 0.20 |
| Glycine USP | 7.500 | 1.50 |
| Total | 500.000 | 100.00 |

*signifies removed during lyophilisation process.

EXAMPLE 13

| Ingredient | Parts by Weight | % by weight of composition |
|---|---|---|
| Purified Water EP/USP* | 413.000 | 82.60 |
| Apomorphine HCl BP/EP | 10.000 | 2.00 |
| Naltrexone HCl | 25.000 | 5.00 |
| Gelatin EP/USNF | 22.500 | 4.50 |
| Mannitol EP/USP | 15.000 | 3.00 |
| Citric Acid EP/USP | 2.500 | 0.50 |
| Aspartame EP/USNF | 5.000 | 1.00 |
| Raspberry Flavour | 2.000 | 0.40 |
| Glycine USP | 5.000 | 1.00 |
| Total | 500.000 | 100.00 |

*signifies removed during lyophilisation process.

EXAMPLE 14

| Ingredient | Parts by Weight | % by weight of composition |
|---|---|---|
| Purified Water EP/USP* | 397.250 | 79.45 |
| Apomorphine HCl BP/EP | 20.000 | 4.00 |
| Naloxone HCl BP/EP | 10.000 | 2.00 |
| Domperidone | 20.000 | 4.00 |
| Gelatin EP/USNF | 22.500 | 4.50 |
| Mannitol EP/USP | 17.500 | 3.50 |
| Citric Acid EP/USP | 1.500 | 0.30 |
| Lemon Lime Flavour | 2.500 | 0.50 |
| Glycine USP | 5.000 | 1.00 |
| Aspartame EP/USNF | 3.750 | 0.75 |
| Total | 500.000 | 100.00 |

*signifies removed during lyophilisation process.

EXAMPLE 15

| Ingredient | Parts by Weight | % by weight of composition |
|---|---|---|
| Purified Water EP/USP* | 219.008 | 87.60 |
| Apomorphine HCl BP/EP | 5.000 | 2.00 |
| Granisetron HCl | 1.117 | 0.45 |
| Gelatin EP/USNF | 10.625 | 4.25 |
| Mannitol EP/USP | 7.500 | 3.00 |
| Citric Acid EP/USP | 1.500 | 0.60 |
| Mint Flavour | 1.500 | 0.60 |
| Glycine USP | 1.250 | 0.50 |
| Aspartame EP/USNF | 2.500 | 1.00 |
| Total | 250.000 | 100.00 |

*signifies removed during lyophilisation process.

EXAMPLE 16

| Ingredient | Parts by Weight | % by weight of composition |
|---|---|---|
| Purified Water EP/USP* | 416.0 | 83.2 |
| Gelatin | 18.0 | 3.6 |
| Mannitol | 13.5 | 2.7 |
| Testosterone undecanoate | 50.0 | 10.0 |
| Aspartame | 2.5 | 0.5 |
|  | 500.00 | 100.0 |

*signifies removed during lyophilisation process.

The complete disclosures of all patents, patent applications and publications are incorporated herein by reference as if each were individually incorporated by reference. The invention has been described with reference to various specific and preferred embodiments and techniques. However, it should be understood that many variations and modifications can be made while remaining within the spirit and scope of the invention.

What is claimed is:

1. A method for the treatment of male erectile dysfunction comprising the step of oral administration of a pharmaceutical composition comprising a carrier and an active ingredient selected from the group consisting of a dopamine agonist, testosterone and mixtures thereof, the composition being in the form of a fast-dispersing dosage form designed to release the active ingredient rapidly in the oral cavity by disintegrating within 1 to 30 seconds of being placed in the oral cavity; and wherein said composition is a solid fast-dispersing dosage form comprising a network of the active ingredient and a carrier, the network having been obtained by subliming solvent from a composition in the solid state, that solid state composition being formed from components comprised of the active ingredient and a solution of the carrier in water, wherein said carrier is inert toward the active ingredient and comprises a matrix forming agent.

2. The method of claim 1 in which the dopamine agonist is apomorphine or a salt thereof.

3. The method of claim 1 in which the active ingredient is present in an amount of from 0.05 to 50 mg.

4. The method of claim 1 which further includes an anti-emetic.

5. The method of claim 4 in which the anti-emetic is present in an amount of from 1 to 120 mg.

6. The method of claim 4 which further includes an opioid antagonist.

7. The method of claim 6 in which the opioid antagonist is present in an amount of from 0.5 to 100 mg.

8. The method of claim 1 in which the active ingredient comprises testosterone.

9. The method of claim 8 in which the testosterone is present in an amount of 10 to 100 mg.

10. The method of claim 3 in which further includes an anti-emetic present in an amount of from 1 of 120 mg.

11. The method of claim 1 in which the active ingredient comprises testosterone.

12. The method of claim 6 in which the active ingredient comprises testosterone.

13. The method of claim 7 in which the active ingredient comprises testosterone.

14. The method of claim 11 in which the testosterone is present in an amount of 10 to 100 mg.

15. The method of claim 12 in which the testosterone is present in an amount of 10 to 100 mg.

16. The method of claim 1 wherein said matrix forming agent comprises gelatin.

* * * * *